United States Patent
Klein et al.

Patent Number: 5,330,268
Date of Patent: Jul. 19, 1994

[54] APPARATUS FOR DETERMINING THE CONDITION OF A PRESSURE TRANSMITTING FLUID

[75] Inventors: Hans-Christof Klein, Hattersheim; Peter Lohberg, Friedrichsdorf; Hans-Joachim Krause, Gottingen/Elliehausen; Arno May, Gottingen; Dietmar Oberdorfer, Gottingen; Ulrich Pluquett, Gottingen, all of Fed. Rep. of Germany

[73] Assignee: Alfred Teves GmbH, Frankfurt Am Main, Fed. Rep. of Germany

[21] Appl. No.: 915,682

[22] PCT Filed: Nov. 28, 1990

[86] PCT No.: PCT/EP90/02037
§ 371 Date: Sep. 14, 1992
§ 102(e) Date: Sep. 14, 1992

[87] PCT Pub. No.: WO91/11707
PCT Pub. Date: Aug. 8, 1991

[30] Foreign Application Priority Data
Jan. 31, 1990 [DE] Fed. Rep. of Germany ....... 4002792

[51] Int. Cl.$^5$ ................... G01N 27/04; G01N 25/56; G01N 25/00
[52] U.S. Cl. ..................... 374/54; 324/694; 324/696
[58] Field of Search ............. 73/295; 374/54; 324/694, 696

[56] References Cited

U.S. PATENT DOCUMENTS

| 3,264,558 | 8/1966 | Heeps | 324/694 |
| 3,522,530 | 8/1970 | Muller | 324/694 |
| 3,943,767 | 3/1976 | Efferson | 73/295 |
| 4,558,456 | 12/1985 | Bezard et al. | 73/295 |
| 4,805,454 | 2/1989 | LeVert | 73/295 |
| 5,028,144 | 7/1991 | Klein | 324/694 |
| 5,044,764 | 9/1991 | Aoki et al. | 73/295 |

FOREIGN PATENT DOCUMENTS

| 3522774 | 1/1987 | Fed. Rep. of Germany | 73/295 |
| 0492750 | 3/1976 | U.S.S.R. | 73/295 |
| 2134260 | 8/1984 | United Kingdom | 73/295 |

*Primary Examiner*—Diego F. F. Gutierrez
*Attorney, Agent, or Firm*—Robert P. Seitter; J. Gordon Lewis

[57] ABSTRACT

An apparatus for determining the boiling temperature of a brake fluid to in turn determine the water content therein includes an electrically heatable sensor element (13) immersed into the fluid under test, a power source (12) supplying a current of a constant amplitude, and a measuring system (15) for measuring the voltage drop on the sensor element (13). A stable cellular convection heat transfer mechanism into the surrounding fluid arises, with the voltage drop across the sensor element (13) being indicative of the boiling point of the fluid. The sensor element is in the form of a linear conductor (13', 20, 21) clamped on either end. The sensor element also may comprise a plurality of linear conductors (13', 20, 21) of this type connected in parallel or in series.

4 Claims, 2 Drawing Sheets

APPARATUS FOR DETERMINING THE CONDITION OF A PRESSURE TRANSMITTING FLUID

BACKGROUND OF THE INVENTION

The present invention is concerned with an apparatus for determining the condition of a pressure transmitting fluid, in particular, for checking or monitoring the water content or the boiling temperature of a hygroscopic brake fluid. Such apparatus typically comprises an electrically heatable sensor element immersed in the fluid to be tested, a power source supplying an electric current of constant magnitude to the sensor, and a measuring device measuring the voltage drop across the sensor element to determine the temperature-dependent resistance of the sensor element. The sensor element is of a configuration and size and the heating current being at a magnitude such that heating of the sensor element over the duration of the period of measurement causes a stable cellular convection to arise in a temperature range below the boiling temperature of the fluid. The voltage drop across the sensor element is an accurate indicator of the water content of the liquid.

An apparatus of the afore-described type is disclosed by German published patent application DE 35 22 774 A1. The sensor element of the apparatus is configured and the current supply devised such that at the time of measurement, a stable cellular convection arises. This requires a heating of the sensor element to a predetermined temperature which is within a temperature range just below the boiling temperature of the fluid to be tested, it being imperative for the sensor element not to be heated to the boiling temperature of the fluid under test.

According to the referenced German application, it is suggested to form the sensor element as a hollow body having an open wall; as a hollow helix; as a perforated tube or the like to favor the formation of convection cells and of the stable cellular convection, respectively, during the measuring time. However, sensor elements of that type are relatively costly which applies, in particular, if a stationary assembly in an automotive vehicle or in each of the wheel brakes of an automotive vehicle, respectively, is desired. Moreover, the requirements placed upon the mechanical stability of the sensor element, in that case, are particularly high.

The invention is, therefore, based on the problem of providing a mechanically stable yet low-cost sensor element for use with an apparatus of the afore-mentioned type, permitting the formation of a stable cellular convection during the measuring process.

SUMMARY OF THE INVENTION

It has been discovered that this problem can surprisingly be solved by a sensor element which is in the form of a very simple linear conductor, e.g. a short length of wire which is fixed at either end in a holder to have mechanical stability. Also, the sensor element may be composed of a plurality of linear conductors of this type connected in parallel or in series The length of wire must be geometrically configured and dimensioned such that convection cells can be formed on all linear conductors i.e., boundary layer stream caused by a stable cellular convection arises. The value of a constant electrical current is determined which when passed through the length of wire will heat the surrounding liquid in a thin layer over the wire so as to establish a boundary layer stream and steady state heat transfer by cellular convection from the wire into the liquid over a range of water content levels in the liquid. The previously determined constant magnitude of electrical current is passed through the wire extended within a liquid having an unknown water content to cause the length of electricity conductive wire to be heated to a temperature varying with the water content level in the liquid. The electrical resistance of the wire at this temperature is determined, and the results of this determination are analyzed by comparison with previously determined electrical resistance values of the length of electrically conductive wire with the constant electrical current magnitude passed therethrough for varying water content levels of the liquid, to thus enable ascertaining the actual water content level of the liquid.

According to an advantageous embodiment of the invention, the sensor element is made of a platinum-/iridium alloy of a 90%/10% composition. The sensor element may be of a length of between 10 and 30 mm, preferably between 15 and 20 mm, and of a diameter of between 30 and 80 $\mu$m, preferably between 40 and 60 $\mu$m.

According to another advantageous embodiment of the invention, the sensor element is approximately vertically disposed in the fluid to be tested. Also, it may be placed into the fluid at a predetermined inclination or at a variable partially vertical inclination for adjusting the measuring characteristics by varying the proportion of the length of the wire enveloped by the boundary layer stream. Finally, it may be favorable in some instances, for the sensor element to be surrounded, at least in part, by a tube open on either end and permitting the formation of an enveloping stream and a stable cellular convection, respectively, between the linear conductor and the tube. A sensor element of that type is relatively insensitive to flow movements in the fluid to be tested. A formation of this type, equally, is of advantage for the construction of hand-guided measuring probes.

DESCRIPTION OF THE DRAWINGS

Additional features, advantages and fields of end-use application will become manifest from the following description of examples of the invention with reference to the drawings, wherein.

DETAILED DESCRIPTION

The apparatus according to the invention is based on the boiling temperature determination with the aid of a sensor element being configured and heated such that a stable so called "cellular convection" heat transfer mechanism without boiling will occur. Such a cellular convection will occur once the sensor element used as the convection element generates a heat amount which, through "laminar convection" (off-flowing heat conduction) no longer can be quickly enough transferred into the surrounding total fluid volume, but which does not yet generate any boiling bubbles. Thin boundary layers are then formed that surround the heating element like an enveloping stream. Accumulated heat is collected within a cell in the stream up to the heating element; the cell itself, through laminar convection, is able to dissipate just as much heat to the outside into the fluid chamber as can be accepted by and distributed in the said chamber per unit of time. The heating element and the environment of the convection cell, hence, behave like a common heating structure which, relative to laminar convection conditions, is in a steady state of thermal transfer to the surrounding fluid. The boundary layer remains stable as long as the temperature on the inner side of the boundary layer is higher by no more than a predetermined amount than it is on the outer side of the fluid remainder. Once the fluid is heated beyond a certain temperature, no convection cell formation will occur, and it is no longer possible to determine the boiling temperature of the fluid with the apparatus of the type with which the invention is concerned. This distribution of the temperature of the accumulated heat occurring within the convection cells, among others, is dependent on the fluid movement within the cell. Such movement, in turn, is determined by the density and viscosity of the fluid and by the buoyancy phenomena.

Figure 1:
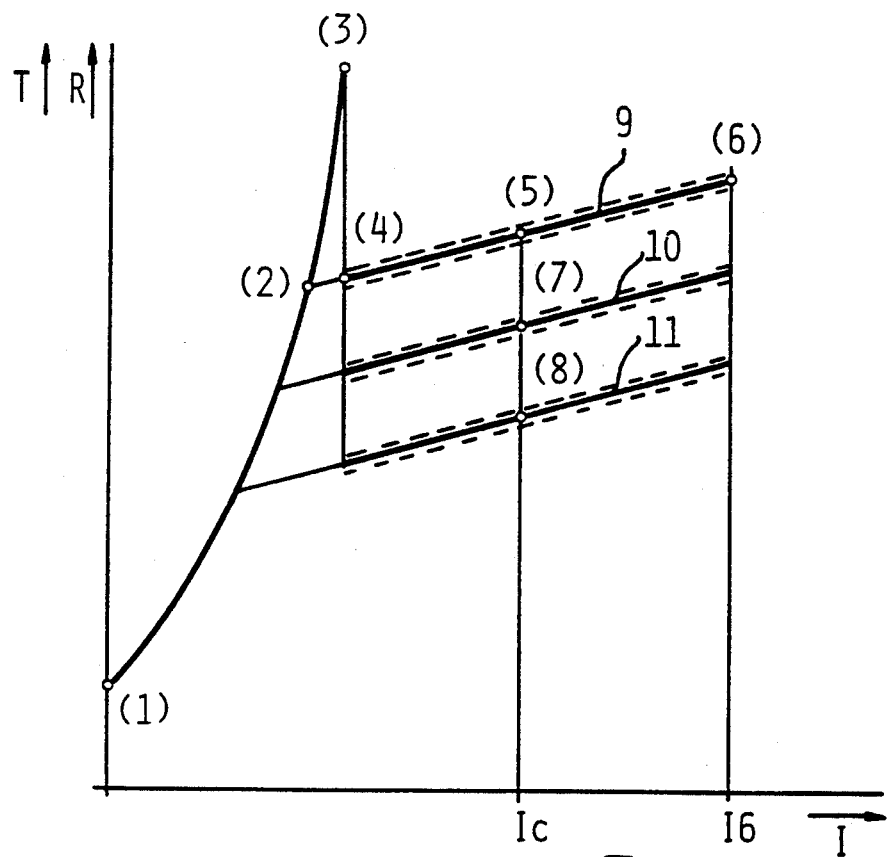
FIG. 1 is a plot of the basic relationship between temperature and ohmic resistance, respectively, and the current in a sensor element of the type according to the invention.

To determine the boiling temperature with the aid of the apparatus according to the invention, the varying heat resistance of the sensor element is analyzed resulting from the transfer of heat into the boundary layer between the heater surface and the surrounding fluid. In hygroscopic brake fluids, the mixture with water causes a specific change in density and viscosity and, hence, in the temperature of the sensor resulting from the accumulated heat. That change is analyzed for determining the boiling temperature. The diagram according to FIG. 1 serves for demonstrating the processes, showing the temperature T or of the corresponding electrical resistance R of the sensor element determining the temperature in response to increasing heating current, I. From the ambient temperature (1), the temperature first rises beyond a value (2), in parabolic form, to assume a maximum (3). This pattern corresponds to the range within which heat transfer occurs exclusively by laminar convection. The characteristic line then assumes a pronounced negative course (3)–(4) to then extend at a low and approximately constant rise to reach point (6). The characteristic line section (4)–(6) is typical for the range of cellular convection which, in the practice of the invention, is analyzed for determining the boiling temperature of the fluid to be tested. Point (5) in the mid part of line sector (4)–(6) marks a favorable operating point.

The triangle (2)–(3)–(4) is referred to as a "bifurcation" zone because the characteristic line, with a rising heating energy, always pursues the (2)–(3)–(4) course, while conversely, it follows the (4)–(2) pattern in skipping point (3). The bifurcation zone characterizes the zone where the afore-described boundary layer starts to form. Sensor elements and heating elements, respectively, showing such a course of the characteristic line, basically, are suitable as convection bodies and sensor elements, respectively, for the apparatus of the invention. A strong bifurcation zone, as a rule, is indicative of an advantageous design of the sensor element.

The temperature level of the characteristic plateau (4)–(6) varies in response to water content of the fluid under test. The characteristic lines 10 and 11 apply to fluids having lower water content and boiling points compared to the fluid of characteristic line 9. Upon delivery of a predetermined constant current Ic, to these fluids a temperature will be reached which varies with water content, i.e., for lower water contents instead of reaching the temperature of working point 5 for characteristic line 9, the temperature of either working point (7) or (8) will be reached (for characteristic line 10 and 11, respectively), AA predetermined electrical resistance and a particular voltage drop, respectively, will thus be experienced across the sensor element for each water content layer.

Figure 2:
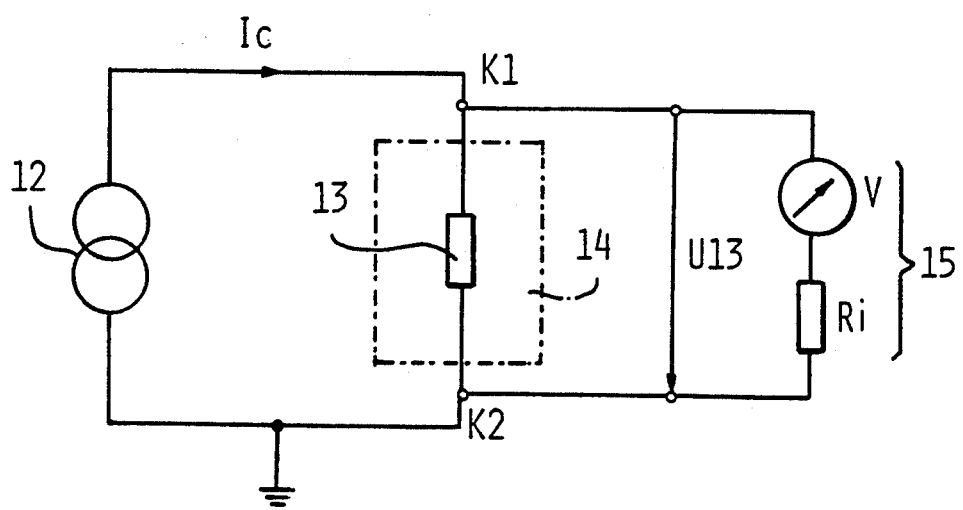
FIG. 2 is a diagrammatic representation of the basic measuring apparatus of the invention.

FIG. 2 shows the basic design of a measuring system suitable for use with the apparatus according to the invention, in which the measuring system substantially comprises a power source 12 supplying a direct or alternating current Ic of a constant amplitude, the sensor element 13 immersed into the fluid to be tested, the volume of which is designated by 14, and a high-ohmic voltage meter 15 connected to terminals K1, K2.

Figure 3:
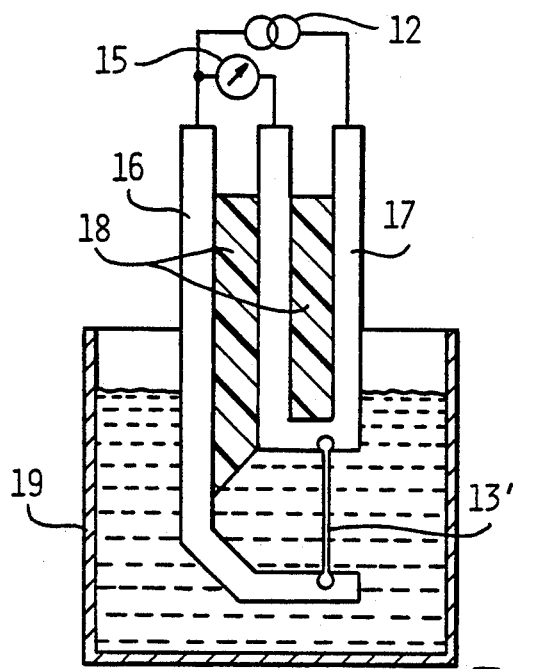
FIG. 3 is a sectional view of a sensor element of the invention in a container of fluid together with a schematic representation of associated apparatus.

FIG. 3 shows a concrete example of an apparatus of the type as provided by the invention, provided with a measuring circuit according to FIG. 2. The elongate linear conductor 13' serving as a sensor element, in this embodiment, comprises a short-length of wire clamped or fixed on both ends. A platinum/iridium alloy Pt/Ir (90%/10%) was used for the wire. The sensor element 13', in this embodiment, is of a length of between 10 and 15 mm and of a diameter of 50 $\mu$m, with the length being selected so as to provide an ohmic resistance in the range of between 1.7 and 2.3 ohms. The operating current for the generation of a stable cellular convection will then be in the range of 1 ampere.

In the embodiment according to FIG. 3, the linear conductor 13' of the apparatus of the invention, is fixed at each end to extend across a gap in a holder comprised of two electrodes 16, 17 of nickel-silver sheet metal embedded into a electrically non-conductive flat supporting body 18. In analogy with FIG. 2, the constant current source was designated by 12, the voltmeter by 15. The sensor element 13' is connected to the electrodes 16, 17 by spot welding. The sensor element 13' is immersed in a container 10 filled with the liquid under test.

Also, it is readily possible to combine two or more similar sensor elements of a simple construction, and to electrically operate the same in a condition connected in parallel or in series. The spatial arrangement and the distance of the individual sensor elements from one another would then have to be so selected as to enable the cellular convection of the invention to form.

Figure 5:
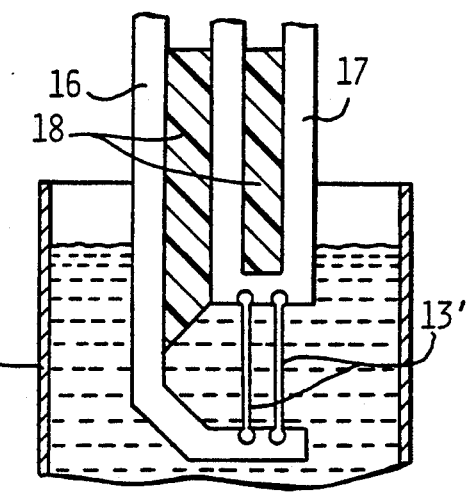
FIG. 5 is a fragmentary sectional view of an alternate embodiment of the sensor element shown in FIG. 3.

For example, additional similar linear conductors 13' could be disposed between the electrodes 16, 17 in parallel and be welded to the electrodes, as shown in FIG. 5.

The basic configuration and arrangement of particularly simple linear conductors are shown in FIG. 4. According to FIG. 4a, the sensor element comprises a short-length linear conductor 20 which, theoretically, can be considered a degenerate helix so stretched that no enclosed interior space is left, with a corrugated or even straight-lined linear conductor being formed in extreme cases. With a predetermined ohmic resistance of a helical heater or sensor element, the operating current requirements for the generation of a cellular convection are at a predetermined ratio to the helix pitch. With a narrow helix, a minimum amount of operating current is required, while a slightly higher amount is needed by a helix degenerated to form a stretched conductor. However, a stretched helix of a low helical inside diameter to wire diameter ratio is of a superior mechanical inherent rigidity which is of substantial advantage to the practical use of a sensor element according to the invention. FIG. 4a shows a so stretched degenerate helix 20. The two end points A and B formed through material reinforcement and a conductance enhanced thereby, define the effective length of the sensor element. FIGS. 4b and c show linear conductors 21 in the form of completely stretched line conductors. According to FIG. 4b, the sensor element has its longitudinal axis vertically arranged while in FIG. 4c, the longitudinal axis is tilted by a predetermined angle vis-á-vis the normal. Either case shows the Schlieren configuration of the enveloping stream 23. In response to the inclination of the linear conductor 21 representing the sensor element, and to the effect involved, of the buoyancy forces on the enveloping stream 23, a predetermined portion of the linear conductor 21 remains within the range of effect of the enveloping stream 23. By changing or adjusting the inclination from the vertical, the characteristic line of the sensor element serving as a measuring element is made variable and can be adapted to predetermined requirements. For example, according to FIG. 4b, the complete sensor element is enveloped by the stream while according to FIG. 4c, a portion of the length dL projects out of the enveloping stream. This fact can be used to convey a varied characteristic to the curve pattern of the line section (4)-(6) of FIG. 1.

Figure 4A:
FIGS. 4a-e are elevational views of various embodiments of the sensor element according to the invention.
Figure 4B:
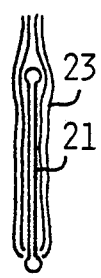
Figure 4C:
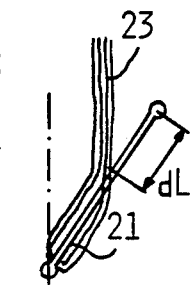
Figure 4D:
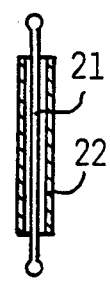
Figure 4E:
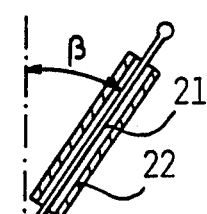

According to the examples of FIGS. 4d and e, the stretched linear conductor 21 representing the sensor element, lies within the enveloping stream and a coaxial tube 22, respectively, tube 22 open on either end so that the enveloping stream is passed between the linear conductor 21 and the inside of the tube 22, the elements of this type are less sensitive to additional flow movements within the fluid under test than sensor elements 21 not provided with such tube enclosures. The sensor elements according to FIGS. 4d and e are particularly suitable for the construction of hand-guided probes. In stationary systems, for example, for assembly into brakes of automotive vehicles, as a rule, the less complex forms of embodiment according to FIGS. 4a-c will do.

We claim:
1. A method of measuring the water content level in a liquid, comprising the steps of:
   determining the constant electrical current magnitude which when passed through a length of a geometrically configured and dimensioned electrically conductive wire which will heat the surrounding liquid in a thin layer over said wire to establish a boundary layer stream and steady state heat transfer by cellular convection from said wire into said liquid over a range of water content levels in said liquid;
   stretching said length of conductive wire between a pair of electrodes, fixing either end of said length of wire so as to be mechanically stabilized and extending the longitudinal axis of said length of electrically conductive wire at an at least partially vertical inclination within said liquid;
   passing said previously determined constant magnitude of electrical current through said wire extended within said liquid to cause the length of electrically conductive wire to be heated to a temperature varying with the water content level in said liquid;
   determining the electrical resistance of said wire at said temperature; and
   analyzing the results of said determination by comparison with previously determined electrical resistance values of said length of electrically conductive wire with said constant electrical current magnitude passed therethrough corresponding to varying water content levels of said liquid to ascertain the actual water content level of said liquid.

2. The method according to claim 1 further including the step of enclosing said length of wire in a tube open at both ends to reduce the effects of any other flow in said liquid on said boundary layer stream.

3. The method according to claim 1 further including the step of varying said vertical inclination of said length of wire to vary the proportion of said length of wire enveloped by said boundary layer stream to establish a desired characteristic relationship between wire temperature produced by said cellular convection and said liquid water content.

4. The method according to claim 1, wherein a plurality of straight lengths of wire are stretched in parallel between said pair of conductive electrodes and disposed in said liquid with the longitudinal axis thereof extending vertically.

* * * * *